United States Patent [19]
DeLange

[11] Patent Number: 5,554,162
[45] Date of Patent: Sep. 10, 1996

[54] METHOD AND DEVICE FOR SURGICALLY JOINING LUMINAL STRUCTURES

[76] Inventor: Gregory S. DeLange, 7934 Pleasant Creek, San Antonio, Tex. 78240

[21] Appl. No.: 349,494

[22] Filed: Dec. 2, 1994

[51] Int. Cl.⁶ .................................................. A61B 17/04
[52] U.S. Cl. .................................................. 606/153
[58] Field of Search ................................. 606/153–154

[56] References Cited

U.S. PATENT DOCUMENTS

| | | |
|---|---|---|
| 4,470,415 | 9/1984 | Wozniak . |
| 4,553,542 | 11/1985 | Schenck et al. . |
| 4,553,543 | 11/1985 | Amarasinghe ........................ 606/153 |
| 4,566,453 | 1/1986 | Masayuki et al. . |
| 4,622,970 | 11/1986 | Wozniak . |
| 4,841,968 | 6/1989 | Dunn et al. . |
| 5,104,399 | 4/1992 | Lazarus .................................. 606/153 |

*Primary Examiner*—Gary Jackson
*Attorney, Agent, or Firm*—Gunn, Lee & Miller, P.C.

[57] ABSTRACT

A method and a device for joining luminal structures. The device is comprised of a bridge, typically cylindrical, having an interior dimension to receive two sets of curved needles and having a series of holes or channels at each end for passage of the needles through the body of the bridge. A plunger, typically activated by an elongated member, urges the needles, point first, through the channels. When the ends of the bridge are inserted into the luminal structures to be joined and the plunger is activated, the needles will move through the channels and through the luminal structure to be joined, allowing the surgeon to grasp the pointed ends of the needles and pull them through the channels and through the luminal structure. On the second ends of the needles are sutures which will ultimately be used to join the two luminal structures.

17 Claims, 5 Drawing Sheets

METHOD AND DEVICE FOR SURGICALLY JOINING LUMINAL STRUCTURES

FIELD OF THE INVENTION

This invention relates to a method and device for surgically joining luminal structures; more particularly, to a method for inserting a unique bridge into an opening in the luminal structure to be joined, the bridge having a means to guide a suture-bearing needle therethrough.

BACKGROUND OF THE INVENTION

The joining of luminal structures in the body is a common and critical procedure in the field of surgery. Luminal structures in the body that may be joined using applicant's unique method and device include components of the vascular, biliary, and genito/urinary systems. Surgical procedures in which bodily luminal structures are joined are typified by the vascular anastomosis, for example, bypassing occluded or stenotic arteries in the leg or heart, repairing lacerated arteries in the wrist, or connecting free muscle flap to a new blood supply to cover exposed bones. Additional uses include, by way of example, reversals of vasectomies, ureteral transection repair, and hepatic duct injury repair.

In the past, the typical technique for joining luminal structures, particularly small blood vessels, is to carefully place interrupted, single sutures circumferentially in close proximity to each other around the ends of the luminal structures to be joined, and securing, such as by tying, the ends of the suture lengths. This is a tedious manual procedure in which the surgeon, using his hands and eyes, aided by magnifiers, carefully guides the needle, bearing the suture, through the delicate and fragile walls of the end of the blood vessel or other luminal structure. The surgeon uses only his eye as a guide and attempts to accurately circumferentially place a first set of sutures in an end of the luminal structure and a second set of suture ends in an end of the second luminal structure, such that the sutures on each end of the luminal structures are a matched set and will join up when the ends are brought together and the sutures tied. Compounding the problem of careful placement of sutures equal distance from one another circumferentially about a luminal end is the dimensions and composition of the luminal structure itself. It is typically quite small, in the range of 1 to 6 mm in diameter and floppy—that is, without rigid walls. Moreover, the surgeons must often join numerous sets of corresponding luminal structures.

What is needed, and has heretofore been unavailable, is a device and method for guiding the suture-bearing needles to ensure proper spacing and placement of the sutures through the walls of the luminal structures to be joined.

Applicant accomplishes this and other objects by providing a simple bridge for insertion into openings of the luminal structures to be joined, the bridge having guide means incorporated therein to guide the needle through the bridge and through the walls of the luminal structures to be joined.

SUMMARY OF THE INVENTION

A method and a device for joining luminal structures. The device is comprised of a bridge, typically cylindrical, having an interior dimension to receive two sets of curved needles and having a series of holes or channels at each end for passage of the needles through the body of the bridge. A plunger, typically activated by an elongated member, urges the needles, point first, through the channels. When the ends of the bridge are inserted into the luminal structures to be joined and the plunger is activated, the needles will move through the channels and through the luminal structure to be joined, allowing the surgeon to grasp the pointed ends of the needles and pull them through the channels and through the luminal structure. On the second ends of the needles are sutures which will ultimately be used to join the two luminal structures.

Applicant provides a bridge, typically but not necessarily cylindrical, the bridge having a first and a second end for insertion into the two openings to be joined.

Applicant further provides within the bridge walls channels or openings which act as guides for the passage of a suture-bearing needle therethrough.

Applicant typically, but not necessarily, provides a bridge bearing a multiplicity of openings or channels therethrough for guiding a multiplicity of needles therethrough, when the end of the bridge has been inserted into the luminal structure.

Applicant also typically, but not necessarily, provides a means for urging needles, typically a cylindrical plunger located and dimensioned to fit within the inside of the bridge, which plunger acts on the second end of the needles to force the pointed end through the channels or openings and through the walls of the luminal structure. The surgeon will then grasp the tips of the needles and manually withdraw them from the bridge and pull a first end of the suture length through the puncture created by the passage of the needle through the luminal structure.

Applicant further provides to the bridge, urging means and guide means, a second set of needles with the second ends of the suture lengths attached thereto, which needles are, as the first needles were, urged through the second luminal structure after the second end of the bridge has been inserted into the opening of the second luminal structure. With the first and second ends of the bridge incorporating substantially similar channels or openings, an almost identical pattern is created in the second luminal opening to join the two luminal structures.

Applicant's unique method provides for joining of the two or more luminal structures, such as blood vessels, by the insertion into openings of the luminal structures to be joined, of means for guiding the needles, followed by urging the needles through the guide means until the needles engage and penetrate through the walls of the luminal structure. Passage of suture-bearing needles through the guide means occurs simultaneously. A similar procedure is carried out by inserting the second end of the guide means into a second luminal structure and inserting needles carrying the second end of those sutures already engaged with the first luminal structure. Tying or otherwise securing the ends of the suture material completes the surgeon's task of approximating the luminal structures.

Applicant's unique method and device provide a means for producing almost identically shaped suture patterns about each of the luminal structures so as to incorporate a tight, clean, symmetrical, and leak-proof surgical joinder of the luminal structures.

To realize the objects and advantages of applicant's unique method and device, applicant makes use of a single, self-contained, removable bridge or bridge which typically contains within needles bearing suture material, as well as a means to urge the needles from the inside out through the walls of the bridge and the luminal structure. The advantages of applicant's unique method and device provided are many, including: providing assurance that all layers of the luminal structure's wall are included in the anastomosis; providing assurance that each suture is at the optimal distance from the luminal structure's end and from each other; providing assurance that the position of each suture on one luminal structure mirrors its counterpart on the other of the luminal structures to be joined; expediting an often long and tedious heretofore manual and eye-guided procedure; facilitating the performance of a vascular anastomosis at often difficult access sites, such as the axilla; and markedly diminishing the necessity of removing adherent connective tissue to the luminal structure or, at least, providing for minimal luminal structure preparation.

DETAILED DESCRIPTION OF THE PREFERRED EMBODIMENT

FIGS. 1a–1e and 2 will illustrate details of one preferred embodiment of applicant's invention contemporaneously with discussing the method in which the device is used. The remaining figures will illustrate alternate preferred embodiments of applicant's device as well as additional details of the embodiments set forth in FIGS. 1a–1e and 2.

Figure 1A:
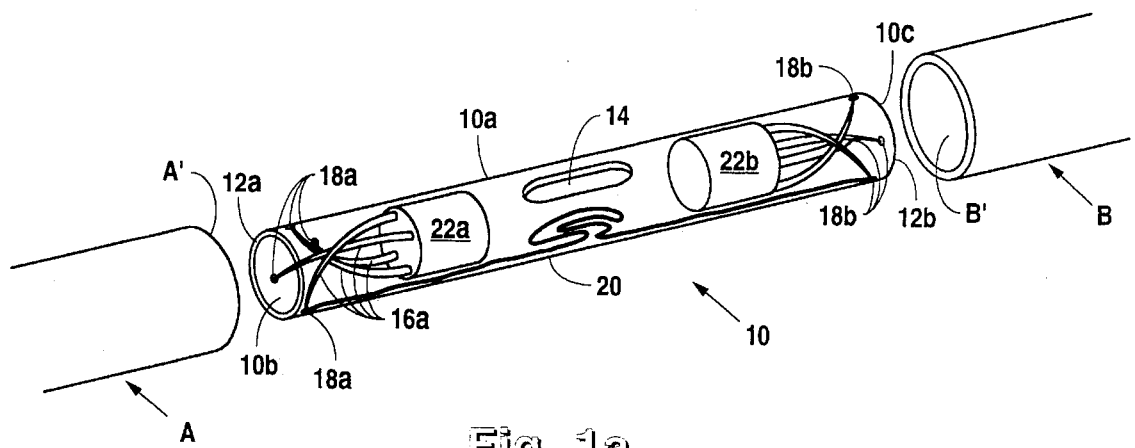
FIGS. 1a through 1c are perspective views illustrating applicant's unique bridge and the method in which it is used to attach luminal structures.

FIG. 1a illustrates a first luminal structure A, typically but not necessarily a blood vessel, having an opening A', typically annular. The intent of the surgeon is to join the first luminal structure A with a second luminal structure B, here a blood vessel dimensioned similar to that of first luminal structure A. Second luminal structure B has an opening B', typically annular. The intent of the surgeon is to surgically join the two luminal structures A and B at their annular openings A' and B' in a clean, tight joinder through the use of needles and sutures of applicant's invention as set forth in more detail below.

Applicant's unique device includes a bridge 10 typically, but not necessarily, cylindrical and having a body 10c typically defined in a hollow interior, the bridge having an open first end 10a and an open second end 10b. The first end 10a and the second end 10b of body 10c are defined by walls forming perimeter 12a and perimeter 12b, respectively.

Further, body 10c of bridge 10 typically, but not necessarily, includes opening 14, which may be located centrally between the first end 10a and the second end 10b, the purpose of which will be set forth in more detail below.

Enclosed within body 10c of bridge 10 near first end 10a is located a first set of needles 16a, each needle of the set having a pointed first end and a second end. Likewise, located near second end 10b and within body 10c of bridge 10 is a second set of needles 16b. Again, the needles of second set of needles 16b have a pointed first end and a second end. As can be seen in FIG. 1a, both of the sets of needles are similarly arranged and are comprised of, typically, the same number of needles. The needles of the sets of needles are typically curved, generally transcribing an arc in the range of 10 to 270 degrees.

Located near either end of the body of bridge 10 are holes or channels. In FIG. 1a, a first set of channels 18a are located annularly about body 10c near first end 10a thereof and provide communication between the interior of the body and the outside thereof. The channels comprising the first set of channels 18a are identical to the number of needles comprising first set of needles 16a and are dimensioned to allow passage of the needle therethrough in a manner more specifically set forth below. The second set of channels 18b is generally identically dimensioned to that of first set 18a. That is, the channels of second set 18b are designed to allow the passage of the needles of second set of needles 16b therethrough. Moreover, the pattern transcribed by second set of channels 18b through body 10c is seen to be substantially identical to the pattern created by first set of channels 18a.

Lengths 20 of suture material are provided, each length connecting a second end of needles of the first set of needles to the second end of similarly positioned needles of the second set of needles.

Note that lengths 20 are routed through holes of first set 16a of needles outside of body 10c through channels of second set of channels 18b to connect to the second end of second set of needles 16b. A first plunger 22a is located within body 10c adjacent the second ends of the needles of first set of needles 16a. The first plunger 22a is dimensioned to fit snugly yet able to slide within the interior of bridge 10.

Likewise, second plunger 22b is cylindrically shaped to fit snugly within the interior bridge 10 near second end 10b thereof. Like first plunger 22a, second plunger 22b is located adjacent the second end of needles of second set of needles 16b.

Figure 1B:
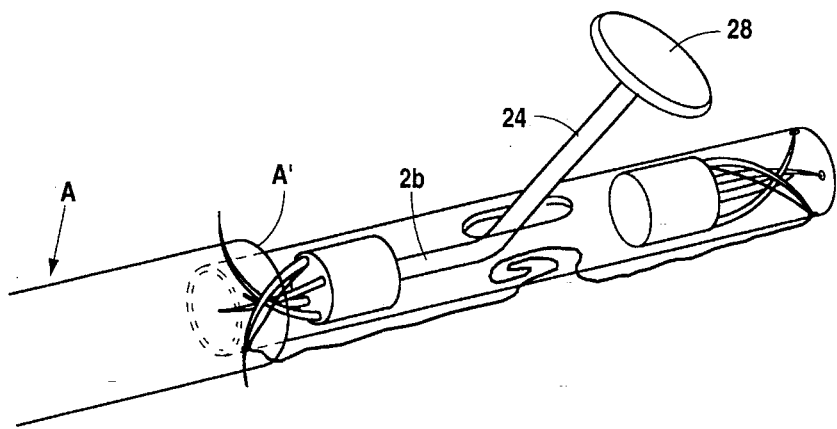
Figure 1C:
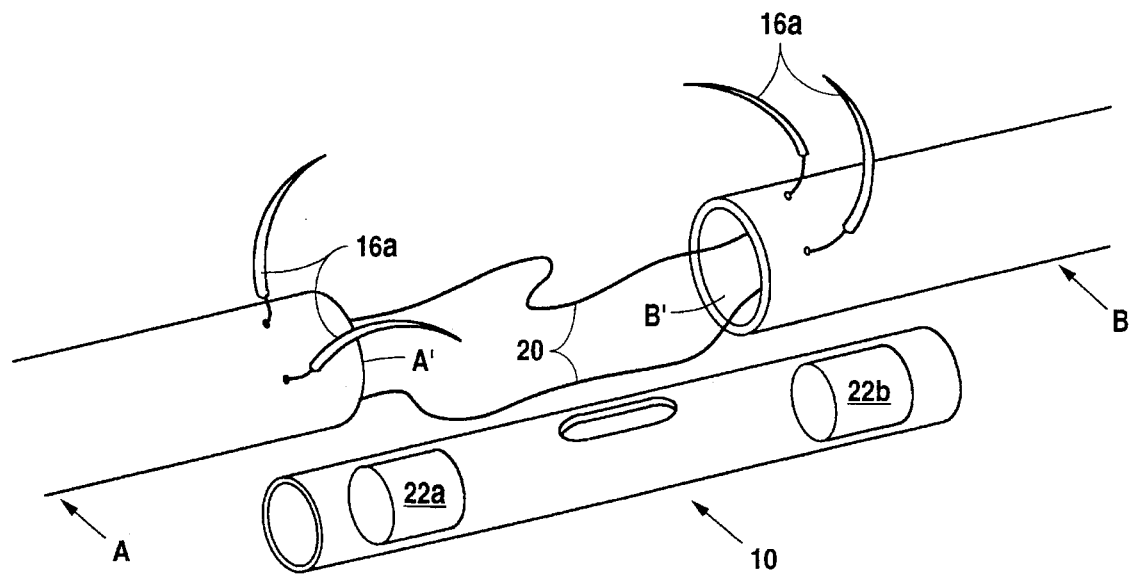

With reference now to FIG. 1b, it is seen that applicant's device includes member 24, typically elongated and dimensioned to fit within opening 14 of body 10c. Member 24 has first end 26 and a second end 28. The member is intended to be fitted against a surface of the plungers as set forth in more detail below.

We turn now to the manner in which applicant's unique device and method is utilized to join first luminal structure A to second luminal structure B. Reference is made to FIGS. 1a–1d and the discussion of the device set forth above. Following location and cleaning of the luminal structures to be joined, by means well known to surgeons, bridge 10 is inserted into the first luminal structure A such that first end 10a slides, typically snugly, within opening A' a distance sufficient to allow the passage of first set of channels 18a through opening A'.

The first ends of each of the needle sets are located with their pointed first ends or tips just adjacent to or within the first set of channels 18a, typically by having been "backed in", second end first, through the channel. The needles of the second set are set likewise, the two plungers having been previously inserted into the open ends of the bridge along with the needles such that the second ends of the needles are flush against the outer surface of the plungers. The suture materials are strung through the channels of the sets such that each needle of the first set 18a is connected by a single length of suture to an identically positioned needle in second set 18b. Applicant's system is now ready for use.

Engagement member 24 is then inserted through opening 14 such that first end 26 is against the inner surface of first plunger 22a. Holding bridge 10 stationary, second end 28 is urged, moving first plunger 22a and the needles of the first set of needles 16a such that each of the needles passes through its channel of first set of channels 18a. Continued urging of first plunger 22a will force the pointed ends of the needles of first set of needles 18a through the walls of first opening A' of first luminal structure A. The surgeon can then manually grasp the first end of the protruding needles and pull the needles completely through the channels of the first set 18a, one by one, until the sutures attached to the second ends of the needles are free of the vessel, as in FIG. 1c. The bridge is then removed.

Figure 1D:
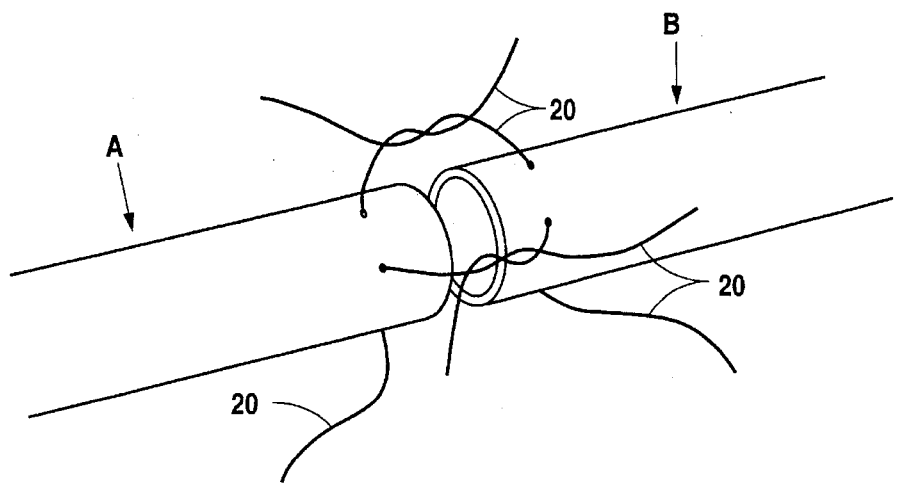
FIG. 1d illustrates the luminal structures to be attached following removal of the bridge therefrom.

This procedure is then repeated with opening B' of second luminal structure B. Care must be taken, however, to prevent the rotation of either bridge 10 or second luminal structure B. This will ensure that the punctures created by the passage of the needles of second set 16b will match up adjacent to the pattern of punctures created by the passage of the first set of needles 16a. After the second ends of suture lengths 20 are free of the walls of the luminal structure, the ends of suture lengths 20 can be left intact or cut adjacent where they attach to the second ends of the needles, the luminal structures brought together and the ends tied, as illustrated in FIG. 1d.

Figure 1E:
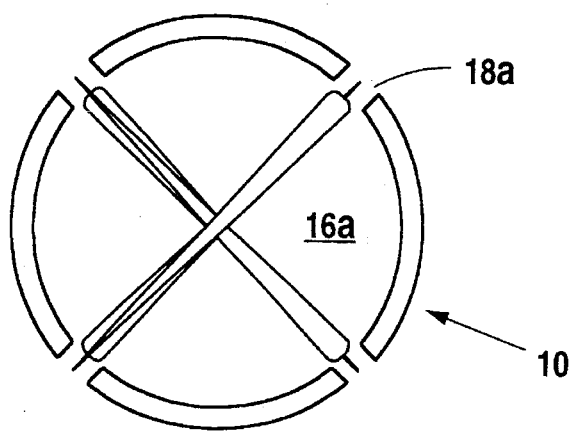
FIG. 1e is a cross-sectional view of the bridge of applicant's invention taken transverse to the longitudinal axis through the channels in the bridge.
Figure 1F:
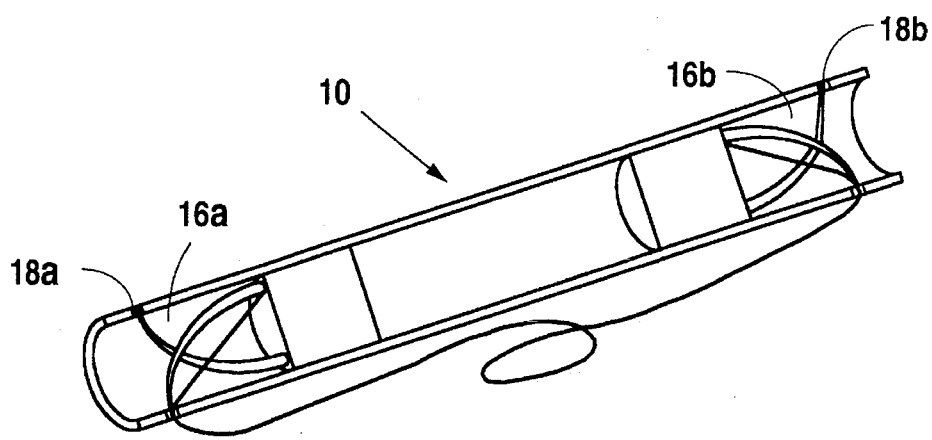
FIG. 1f is a cross-sectional view, in perspective, taken along the longitudinal axis of applicant's invention.

FIGS. 1e and 1f illustrate a cross section of the plunger 10 transverse to the longitudinal axis through first set of channels 18a and a cross section parallel to the longitudinal axis. Both illustrations set forth the manner in which first and second set of needles 16a and 16b, respectively, engage channels 18a and 18b, respectively.

Figure 2:
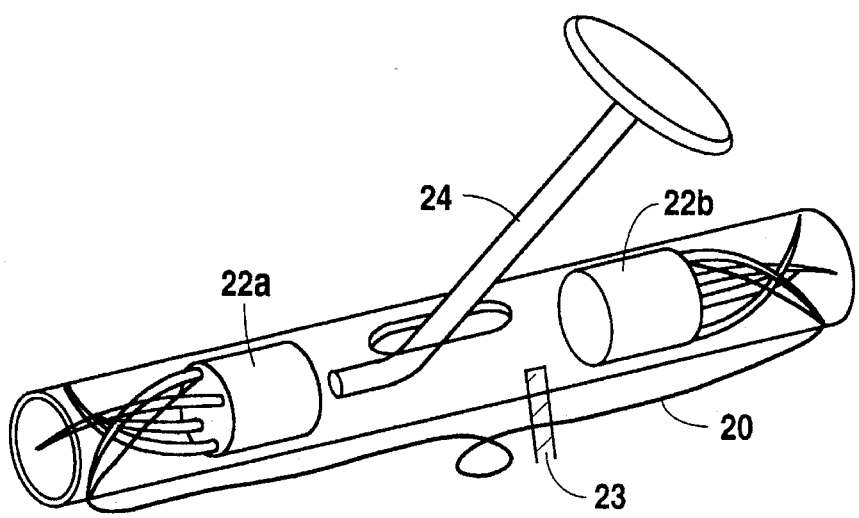
FIG. 2 is a perspective view of applicant's invention.

FIG. 2 illustrates a length of tape 23 which may be used to keep suture lengths 20 (here illustrating only one length for the sake of clarity, it being understood that each needle pair is connected by a suture length) secured to or near the bridge. Glue, elastic bands, or other suitable material may also be used.

Figure 3A:
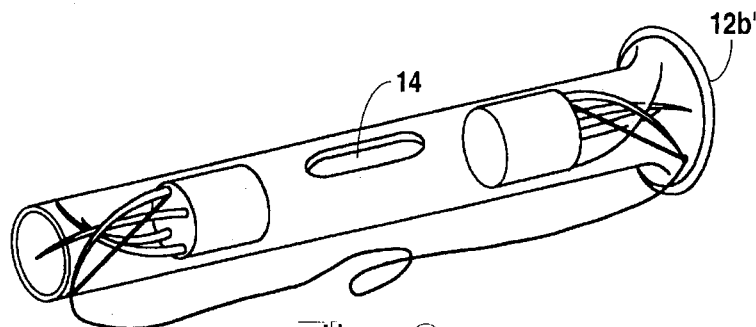
FIG. 3a is a perspective view of applicant's present invention with a flanged end.
Figure 3B:
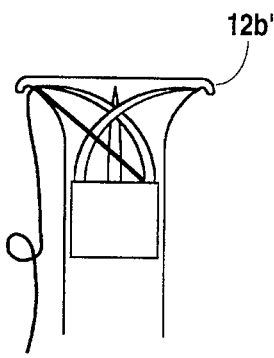
FIG. 3b is a side view of applicant's present invention with a flanged end.
Figure 3C:
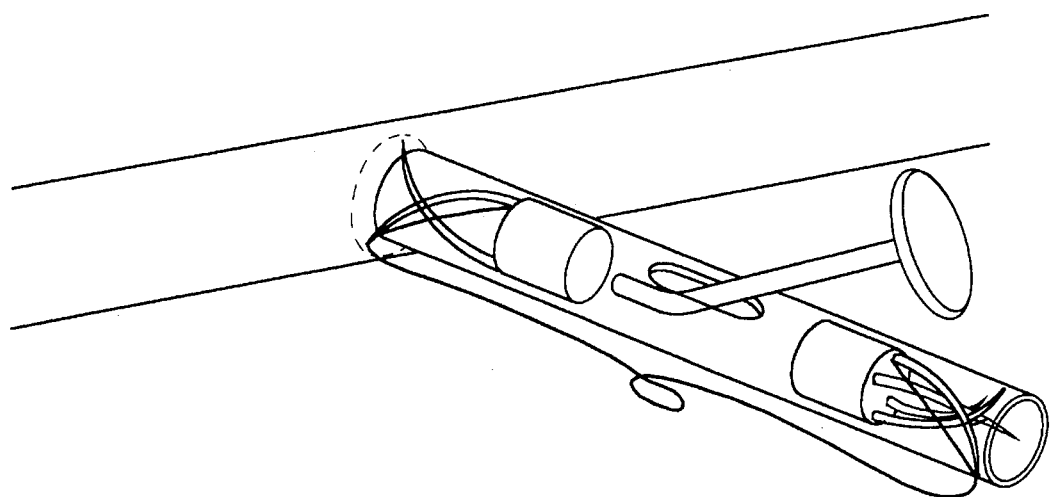
FIG. 3c is a perspective view of applicant's present invention of the flanged end illustrating its insertion into a luminal structure.

While FIGS. 1a and 1b illustrate applicant's system utilized in joining two luminal structures end to end, applicant's system may be used to join luminal structures end to side, as illustrated in FIG. 3c.

A slight modification may be preferable here and is illustrated in FIGS. 3a, 3b and 3c. This modification is incorporated into the shape of perimeter 12b', here having walls defining a flange 12b. This type of perimeter may be advantageous in certain scenarios, for example, an end to side anastomosis, as illustrated in FIG. 3c.

Figure 4:
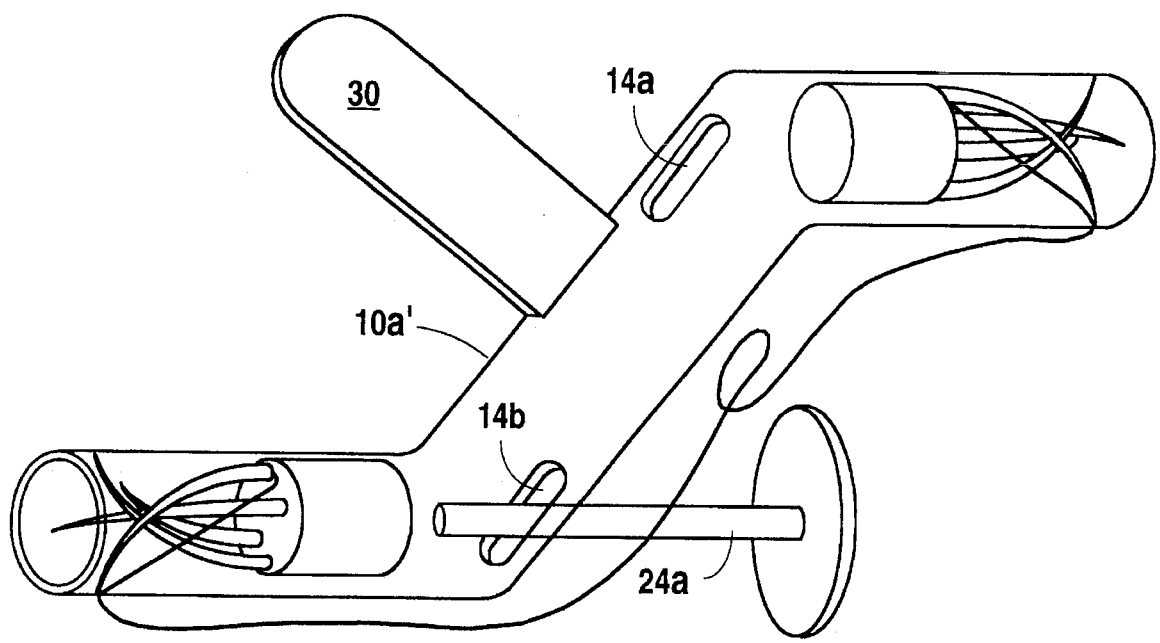
FIG. 4 is a perspective view of an alternate preferred embodiment of applicant's present invention.

FIG. 4 represents an alternate preferred embodiment of applicant's bridge 10. The primary difference in this embodiment is the non-linear body 10a'. This embodiment has two openings 14a and 14b for insertion of member 24a therein. Note here that member 24a is straight whereas the embodiment illustrated in the previous drawings is curved. Any of the embodiments illustrated may be provided with a handle 30 to help stabilize the bridge during use.

Figure 5A:
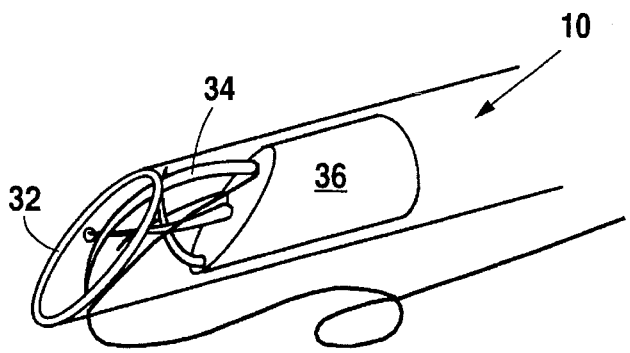
FIG. 5a is a perspective view of an alternate preferred embodiment of applicant's present invention having a tapered end.
Figure 5B:
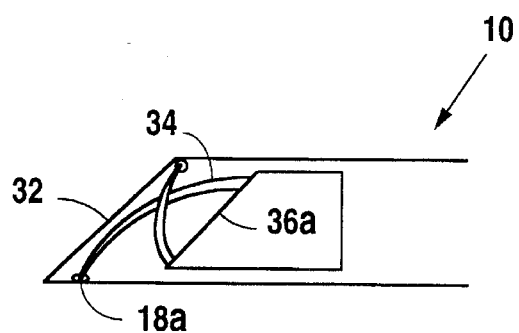
FIG. 5b is a side elevational view of an alternate preferred embodiment of applicant's present invention having a tapered end.

FIGS. 5a and 5b illustrate yet another alternate preferred embodiment of applicant's bridge 10. This particular embodiment is provided with a tapered end 32 and is useful when luminal structures to be joined are diagonally cut rather than straight cut. Note that needle set 34 is provided with individual needles in various lengths. This, in conjunction with the use of tapered plunger 36 having tapered surface 36a engaging the second end of the needles comprising needle set 34 allows the use of first set of needle channels 18a which themselves will lie in a diagonal or tapered plane, typically being parallel to the plane of tapered end 32.

Many variations can be made of applicant's present invention. Among those include varying the number of needles in a needle set. The needles themselves may vary in length. The outside diameter of the bridge may vary between 0.5 mm and 8.5 mm (preferred). The invention and claims set forth herein is intended to include any dimensions, however. Further, it is intended that the bridges may come in sets, the sets having a range of outside diameters typically between 0.5 mm and 8.5 mm, (preferred), providing the surgeon with a suitable size for most applications.

Terms such as "left," "right," "up" "down," "bottom," "top," "front," "back," "in," "out," and like are applicable to the embodiments shown and described in conjunction with the drawings. These terms are merely for purposes of description and do not necessarily apply to the position or manner in which the invention may be constructed for use.

Although the invention has been described in connection with the preferred embodiment, it is not intended to limit the invention's particular form set forth, but on the contrary, it is intended to cover such alternatives, modifications, and equivalences that may be included in the spirit and scope of the invention as defined by the appended claims.

What is claimed is:

1. A system for surgically joining at least two luminal structures, the system comprising:

a bridge having walls defining an interior space, a first end and a second end, and a body, said body being between said first end and second end, said bridge capable of being inserted, at least partially, into the luminal structures;

a first needle having a pointed first end and a second end, said needle dimensioned to be fitted into the interior of said bridge;

suture material for engaging the second end of said first needle;

channel for guiding said first needle through said bridge into the luminal structures to be joined;

wherein one end of said bridge is at least partially inserted into an end of one of the luminal structures to be joined for receipt of said first needle through said guiding means and through the walls of one of the luminal structures.

2. The system as set forth in claim 1 further including means for urging said first needle through said guide means.

3. The system as set forth in claim 1, wherein said channels include a first group of channels in the first end of said bridge and a correspondingly arranged second group of channels in the second end of said bridge.

4. The system as set forth in claim 1 further including a second needle, said second needle having a pointed first end and a second end, said second needle capable of being fitted into the interior of said bridge.

5. The system as set forth in claim 4, wherein said suture material includes a first section having a first end and a second end, the first section for attaching the first end thereof to the second end of said first needle and the second end thereof to the second end of the second needle, said first and said second needle now defining a first joined needle pair, said urging means further capable of urging said second needle through the channels in the walls of said bridge.

6. The system as set forth in claim 5 further including a multiplicity of needles and a multiplicity of suture material sections, the needles of the multiplicity of needles and the sections of the multiplicity of needle sections forming a multiplicity of joined needle pairs as the first needle pair.

7. The system as set forth in claim 6, wherein said urging means is capable of urging simultaneously the first needles of said multiplicity of joined needle pairs through the channels of the walls of the bridge.

8. The system as set forth in claim 7, wherein said multiplicity of joined needle pairs includes a first set comprising the first needles of the pairs and a second set, the second set comprising the second needles of the pairs, the two sets located at opposed ends of the bridge.

9. The system as set forth in claim 8, wherein an end of said bridge is either tapered or straight.

10. The system as set forth in claim 9, wherein said bridge has an opening in the body thereof and wherein said urging means is operable on said multiplicity of pairs through the body opening.

11. The system as set forth in claim 10, wherein the body of said bridge has indicia thereon.

12. The system as set forth in claim 10, wherein the sections of said suture material include means to discriminate one from the other.

13. The system as set forth in claim 10, wherein said bridge is substantially hollow and said urging means includes a pair of plungers shaped to fit flush against the inner surface of the walls of said bridge, the first of the pair of plungers for engaging the first set of the multiplicity of joined needle pairs, the second plunger of the pair of plungers for engaging the second set of the multiplicity of joined needle pairs, said urging means further including an elongated member having a first end and a second end, the first end for inserting through the body opening of said bridge and the second end for grasping by the user, wherein an axial force, applied to the elongated member, will urge either of the pair of plungers against the needles of the joined needle set to urge the needles through the walls of said bridge and through the walls of the luminal structure.

14. The system as set forth in claim 13, wherein said needles of said multiplicity of joined needle pairs are curved, the curve transcribing an arc of between 10 and 270 degrees.

15. The system as set forth in claim 13, wherein at least some of said needles are different lengths than other of said needles and wherein said plungers have at least one beveled surface.

16. The system as set forth in claim 1, wherein said bridge has a body defining multiple, non-linear axes.

17. The system as set forth in claim 8, wherein an end of said bridge is open or closed.

* * * * *